United States Patent [19]

Jackson

[11] 4,429,856

[45] Feb. 7, 1984

[54] INFLATION VALVE

[75] Inventor: Isaac S. Jackson, Greenwich, N.Y.

[73] Assignee: Mallinckrodt, Inc., St. Louis, Mo.

[21] Appl. No.: 332,335

[22] Filed: Dec. 18, 1981

[51] Int. Cl.³ ............................................. F16L 37/28
[52] U.S. Cl. ................................. 251/149.1; 137/843;
   604/247; 604/283
[58] Field of Search ....................... 137/843; 251/149.1,
   251/149.6, 349; 604/247, 283

[56] References Cited

U.S. PATENT DOCUMENTS

| | | | |
|---|---|---|---|
| 2,299,643 | 10/1942 | Moody | 251/149.1 |
| 3,192,949 | 7/1965 | De See | 137/540 |
| 3,385,301 | 5/1968 | Harautuneian | 137/843 |
| 3,481,310 | 12/1969 | Alburger | 137/843 |
| 3,534,771 | 10/1970 | Eyerdam et al. | 137/516.25 |
| 3,726,282 | 4/1973 | Patel | 137/525 |
| 3,831,629 | 8/1974 | Mackal et al. | 137/525 |
| 4,275,907 | 6/1981 | Hunt | 251/149.1 |

Primary Examiner—A. Michael Chambers
Attorney, Agent, or Firm—Bernard, Rothwell & Brown

[57] ABSTRACT

An inflation valve includes a valve body formed of a suitable rigid material and having a longitudinal passage therethrough. Internally the valve body includes an inwardly extending annular member for supporting the valve element and providing a valve seat. This annular member has a predetermined longitudinal dimension between a transverse wall at one end and the base of the valve seat at the other end. The valve includes a valve element made of such size as to move freely within the aforementioned longitudinal passage. It includes a nose portion for engaging the valve seat at one side of the aforementioned annular member on the valve body and an enlarged portion for engaging the transverse wall. The valve element is dimensioned so that the distance between the nose portion of the valve element and the enlarged portion thereof is slightly less than the aforementioned longitudinal dimension of the valve body between the transverse wall and the base of the valve seat. The valve element is made of a flexible elastic material so that it may be compressed upon assembly. During assembly, the nose portion of the valve is forced through the passage of the annular member until this nose portion passes just beyond the valve seat; during this time the enlarged portion is compressed against the transverse wall because of the slightly lesser dimension of the valve element. Upon release of the assembly pressure, the resilience of the flexible valve element causes the nose portion thereof to be urged firmly against the valve seat in reliable sealing engagement.

10 Claims, 4 Drawing Figures 4,429,856

INFLATION VALVE

BACKGROUND OF THE INVENTION

1. Field of the Invention

This invention relates to one-way or check valves and, more particularly, to such valves for use as inflation valves employed with catheters.

2. Description of the Prior Art

Catheters have a variety of uses in conducting fluids to or from body cavities. In many cases catheters are provided with a cuff including an inflatable balloon suitable for engaging and sealing the wall of a body passage so as to limit passage of fluid to or from the body cavity to that passing through the catheter. For example, a tracheal catheter may be designed for insertion through the trachea and may include an inflatable balloon near the distal end for engaging and sealing the tracheal passage.

It is important that the balloon be easily inflated and that it remain in the inflated condition for the desired length of time. For example, a tracheal catheter may be employed in connection with a surgical procedure extending over a significant period of time, and it is necessary that the balloon remain reliably inflated throughout this time.

For this purpose it is conventional to provide a one-way, or check, valve in a tube connected to the balloon for inflation thereof. It is desirable that this check valve, which in this specification will hereafter also be referred to as an inflation valve, be easily actuated when it is desired to supply fluid to the aforementioned balloon of the catheter or when it is desired to discharge the fluid therefrom, and it is desirable that the valve remain reliably sealed during the intervening period.

It is increasingly common that catheters of this type are intended to be disposable after a single use. Accordingly, it is desirable that such devices be of simple construction and be inexpensive to manufacture. These requirements, of course, apply to the inflation valve which forms part of the disposable catheter. Many prior art inflation valves have involved three or more parts and have involved significant cost in manufacture and assembly. The prior art does include some two-piece inflation valves but these prior art two-piece valves have involved manufacturing and assembly problems which increased the cost and make them less desirable, therefore, for use as disposable items.

The valve of the present invention employs a highly simplified two-piece construction which enables the components of the valve to be manufactured easily and at low cost and which is constructed so as to make the assembly of the two parts of the valve simple and easy. Further, the construction is such that the valve element seats firmly so as to insure against undesired leakage of fluid therethrough but is easily moved to its open position when desired so as to provide for passage of fluid.

Accordingly, it is an object of this invention to provide a check valve, particularly for use as an inflation valve in a disposable catheter, which is simple and economical in construction and assembly.

It is a further object of this invention to provide such a valve which is formed from a minimal number of parts.

It is still another object of this invention to provide such a valve which, despite its simplicity and low cost, is effective in preventing leakage of fluids.

SUMMARY OF THE INVENTION

In carrying out the invention, in one form thereof, the inflation valve includes a valve body formed of a suitable rigid material, preferably a suitable plastic. The valve body includes a longitudinal passage therethrough, and this passage is formed at one end with a tapered construction for receiving a suitable luer tip syringe. Internally the valve body includes an inwardly extending annular member for supporting the valve element and providing a valve seat. This annular member has a predetermined longitudinal dimension between a transverse wall at one end and the base of the valve seat at the other end. The valve element is made of such size to move freely within the aforementioned longitudinal passage. It includes a nose portion for engaging the valve seat at one side of the aforementioned annular member on the valve body and an enlarged portion for engaging the transverse wall. The valve element is dimensioned so that the distance between the nose portion of the valve element and the enlarged portion thereof is slightly less than the aforementioned longitudinal dimension of the valve body between the transverse wall and the base of the valve seat. The valve element is made of a flexible elastic material, preferably a suitable elastomer, so that it may be compressed upon assembly. During assembly, the nose portion of the valve is forced through the passage of the annular member until this nose portion passes just beyond the valve seat; during this time the enlarged portion is compressed against the transverse wall because of the slightly lesser dimension of the valve element. Upon release of the assembly pressure, the resilience of the flexible valve element causes the nose portion thereof to be urged firmly against the valve seat in reliable sealing engagement.

DESCRIPTION OF THE PREFERRED EMBODIMENT

Figure 1:
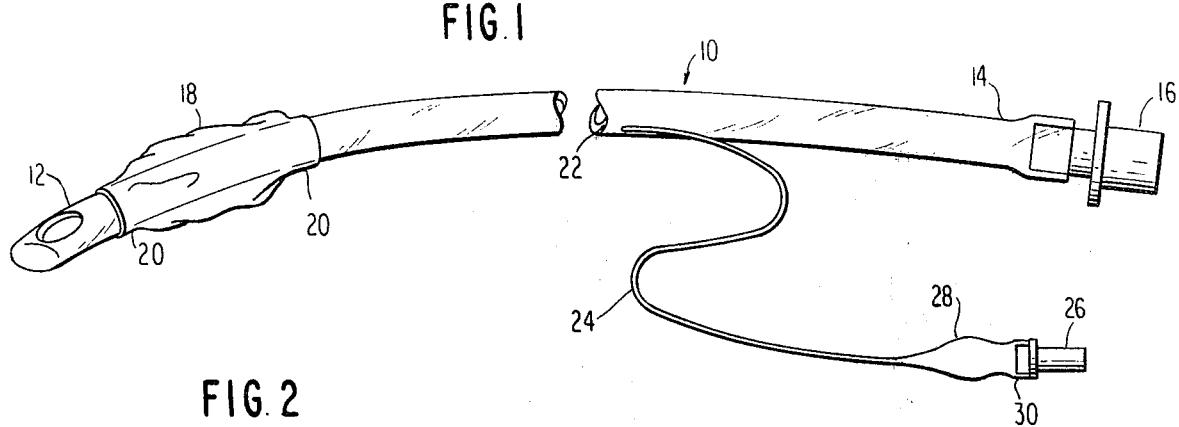
FIG. 1 is a view of a cuffed catheter incorporating the check valve of this invention.

In carrying out this invention, in one form thereof, the one-way or check valve is employed as an inflation valve and is incorporated in a disposable catheter shown in FIG. 1. The catheter, which is of conventional construction, includes a tube 10, which normally is of a suitable translucent plastic. In the particular form of catheter shown the tube 10 is an endotracheal tube intended to be inserted through the trachea and to provide for passage of fluid to and from a body cavity, such as the lungs. The tube includes a distal end 12 and a proximal end 14. The proximal end is provided with a suitable adapter 16 for connection to any suitable medical device for supplying fluid to the body cavity or withdrawing fluid therefrom.

An inflatable cuff 18 is positioned on the exterior of the tube 10 near the distal end thereof. The ends 20 of the cuff 18 are sealed to the exterior wall of the tube 10. In a conventional manner a lumen 22 is formed in the wall of the tube 10 to provide a passage therethrough which includes an opening at the end thereof extending through the exterior wall of the tube 10 within the cuff 18.

In order to provide for the supply of a fluid, such as air, through the lumen 22 for inflating the cuff to place the cuff in sealing relationship against the wall of the treachea, a flexible tubular element 24 is connected at one end to the proximal end of the lumen 22 through a passage formed in the exterior wall of the tube 10 and communicating with the lumen 22. Connected to the other end of the tubular element 24 is a one-way check valve 26 constructed in accordance with this invention. The valve 26 is connected to the tubular element 24 by means of a somewhat bulbous adapter 28, which is formed of a flexible plastic material and includes an enlarged end 30 adapted to be received on the exterior of the body of the valve 26 in sealing relationship therewith.

The valve 26 is a one-way or check valve which is constructed as to permit flow of fluid therethrough to the cuff 18 but to block return flow of fluid from the cuff during the period when it is desired that the cuff remain in its inflated condition.

Figure 2:
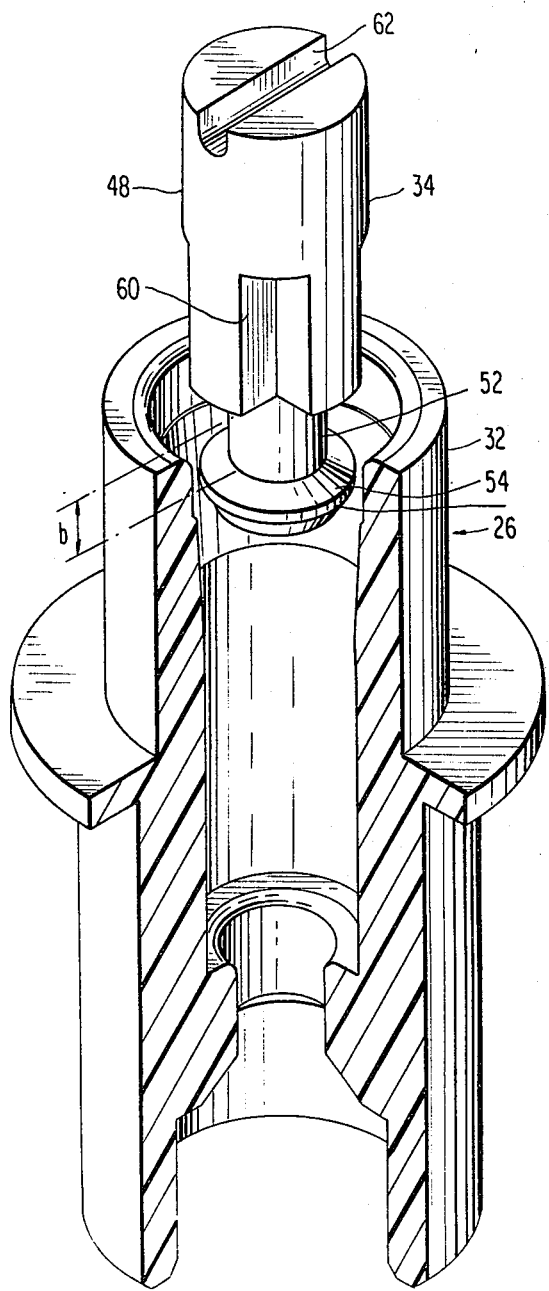
FIG. 2 is an enlarged sectional view of the valve in its open position, showing in phantom the tip portion of a luer syringe actuating the valve.
Figure 3:
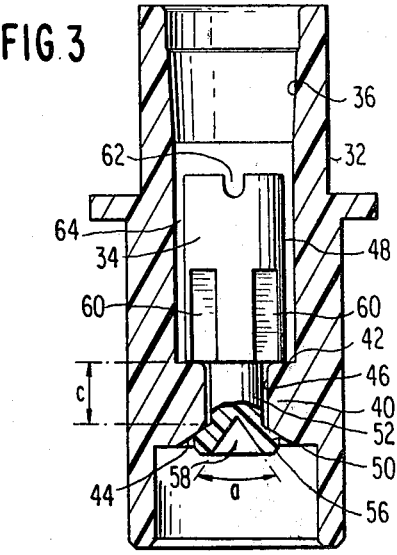
FIG. 3 is a view similar to FIG. 2 but showing the valve in its closed position.
Figure 4:
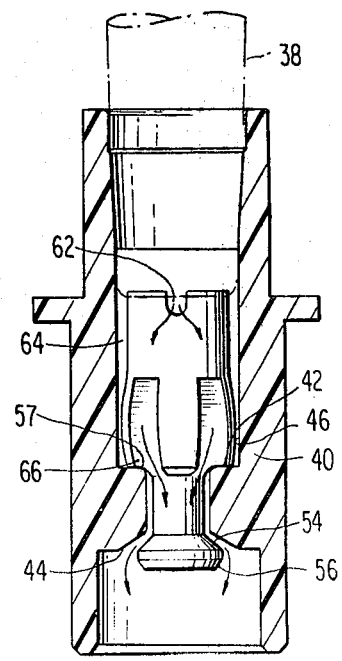
FIG. 4 is an enlarged exploded view showing the two components of the valve positioned for assembly.

The details of the valve and its assembly are shown in FIGS. 2, 3, and 4. As there shown, the valve is of particularly simple construction and comprises only two elements, an outer valve body 32 and an inner valve element 34 which is assembled within the valve body 32. The valve body 32 is a hollow, generally cylindrical member which is formed of a rigid plastic material, for example, polyvinyl chloride (PVC) or acrylonitrile-butadiene-styrene (ABS). The valve body 32 is formed with a tapered wall 36 at one end for receiving the tapered tip of a luer syringe 38. The valve body is formed internally to include intermediate its ends an annular member 40 which extends inwardly from the interior wall of the valve body 32. The annular member 40 is formed to provide at the upper end thereof (as viewed in FIGS. 2, 3 and 4) a flat transverse wall 42. The annular member 40 is provided at its other or lower end with an inclined valve seat 44. A central passage 46 is provided through the annular member 40 for receiving the valve element 34 and for providing for passage of fluid through the valve 26.

The valve element 34 is formed to be received within the hollow interior of the valve body 32. The valve element 34 is formed of an elastic material for reasons which will become apparent as this description proceeds. The preferred material for the valve element 34 is silicone rubber because it has good elongation characteristics and good resistance to heat, chemicals and ozone, but other materials, such as neoprene, may also be used. The valve element 34 includes an upper enlarged generally cylindrical portion 48 having an outer diameter slightly less than the inner diameter of the valve body 32. The valve element further includes a lower portion 50 and an intermediate portion 52 connecting the portions 48 and 50 and received within the central passage 46 in the annular member 40.

The lower portion 50 is formed to provide an inclined surface 54 generally conforming to the slope of the valve seat 44 and being arranged in the closed position of the valve to engage the seat 44. To facilitate assembly of the element 34 witin the valve body 32 the lower portion 50 is provided at its lower end with a tapered portion 50, and the wall 42 of the annular member 40 of the valve body is chamfered, as shown at 57. To further facilitate assembly of the valve element the lower portion 50 is formed, as shown in FIG. 3, to include a conical recess 58. The provision of this conical recess 58 permits the outer edges of the lower portion 50 of the valve element 34 to be squeezed inwardly to facilitate movement through the narrow passage 46 during assembly of the valve element. In one referred embodiment of this invention the recess 58 has an included angle "a" of approximately 74°.

The upper portion 48 of the valve element 34 is formed in the lower section thereof of generally cruciform cross-section so as to provide four longitudinal recesses, two of which are shown at 60 in FIG. 3, providing for passage of fluid from the upper end of the valve body into the central passage 46. The top surface of the portion 48 is provided with a transverse semicylindrical groove 62 which provides for passage of air from the tip of the luer syringe into the space 64 between the upper portion of the valve element and the adjacent interior wall of the valve body.

It is important to the satisfactory seating and operation of the valve that the annular member 40 and the intermediate portion 52 of the valve element have the proper dimensional relationship. Thus, it is important that the longitudinal dimension "b" of the intermediate portion 52 of the valve element in its unstressed condition be less than the longitudinal dimension "c" of the valve body between the transverse wall 42 and the valve seat 44. In one specific embodiment of the valve the dimension "c" is 0.088", and the dimension "b" is 0.073". Further in this specific embodiment of the valve the central passage 46 through the annular member of the valve body 32 has a diameter of 0.093" and the diameter of the intermediate portion 52 of the valve element is 0.078". This latter relationship provides adequate space for passage of fluid through the passage 46 between the wall of the annular member 40 and the intermediate portion 52 of the valve element.

The two components of the valve 26 are easily manufactured with conventional apparatus. The valve element 34 is easily assembled within the valve body 22 by the use of a simple tool but, once assembled, is firmly retained in its assembled position. Should it be desired to disassemble the components for any reason this is also easily and simply effected.

To assemble the two components of the valve, the valve element 34 is placed within the valve body 32 from the direction generally shown in FIG. 4. To facilitate assembly a suitable lubricant, for example a water soluble silicone such as that sold by General Electric Company under the designation SM-2028, is applied to the valve element. Once the lower surface 56 rests on the transverse wall 42, the valve element may be forced into its assembled position by the application of pressure through the use of a simple tool applied to the upper surface of the valve element, a downward force, as viewed in FIGS. 2, 3 and 4, being exerted on the valve element. This force causes compression of the lower portion 50 of the valve element 34, which, as described above, is made of a flexible elastic material, so that the portion 50 is squeezed through the passage 46 in the annular member 40 of the valve body 32. The compression for the portion 50 is facilitated by forming this portion with a conical internal recess 58 which better permits the squeezing of the outer portion of the element 50 through the narrower passage 46. The compression of the lower portion 50 for such assembly is further facilitated by the forming of the lower edge thereof with a tapered surface indicated at 56 and the forming of the transverse wall with a chamfer, indicated at 57, which the tapered surface 56 engages during its initial contact.

As indicated in the description above, the dimension "b" is smaller than the dimension "c", but the valve element is of flexible elastic material and the exertion of the downward force by the tool at the transverse passage 62 causes a squeezing or deformation of the valve element in the region indicated at 66 in FIG. 2 so as to permit the lower portion 50 to pass beyond the central passage 46. Once past the central passage 46 the lower portion 50 resumes its normal shape which exceeds the diameter of this central passage. When the assembly pressure exerted on the top surface of the valve element is then released, the elasticity of the material of the valve element causes the portion 54 thereof to be urged firmly into engagement with the valve seat 46, as shown in FIG. 3, thereby effecting a sealing of the passage through the valve. Should it be desired to disassemble the valve element for any reason this can be done by exerting an upward pressure in the center of the recess 58 which effects a compression of the lower portion 50, allowing its movement upwardly through the central passage 46 for disassembly.

In use, when it is desired to inflate the cuff 18, the tip of the luer syringe 38 is inserted in the tapered upper portion 36 of the valve body and into engagement with the upper end of the valve element 34. Downward pressure may be exerted on the syringe to cause the valve element 34 to be moved downwardly to the position shown in FIG. 2 but, in the form of invention disclosed, the pressure of this fluid transmitted from the syringe will itself move the valve to the open position shown in FIG. 2. In this open position of the valve, fluid, such as air or other suitable gas, passes from the syringe through the transverse passage 62 downwardly through the passage 64 between the upper portion 48 of the valve element and the interior wall of the valve body, through the passages formed by the recesses 60, into the passage 46 and then between the seat 44 and the inclined surface 54 of the lower portion of 50 of the valve element into the adapter 28 and through the tubular element 24 and lumen 22 to the interior of the cuff 18. The path of the fluid through the valve 26 is indicated by the arrows in FIG. 2. Once the cuff has been inflated to the desired pressure the syringe is withdrawn and the resilience of the material of the valve element 34 immediately causes the tapered surface 54 of the valve element to firmly engage the seat 44, blocking passage of fluid therethrough and insuring that the cuff remains in its inflated state through the duration of any medical procedure which may be involved. With some catheters, such as a Foley urethral catheter, sterile water may be employed in lieu of the air or other suitable gas, discussed above, but some dimensional changes might be required. When it is desired to deflate the cuff, the valve element 34 is moved downwardly to the open position shown in FIG. 2 by mechanically exerting downward force on the valve element.

It can be seen from the drawing and the above description that the inflation valve of this invention is of simple and inexpensive construction, is easily assembled, and provides an effective seal in a simple and inexpensive manner. It thus is particularly useful in connection with disposable catheters and similar disposable medical tubes which are designed for a single use and where it is, therefore, desirable that the cost be as low as possible but nevertheless that the components be effective to insure satisfactory performance of their necessary functions.

While a specific construction of the inflation valve of this invention has been illustrated and described, it is not intended that the invention be limited to the particular details of construction as shown and described and it is intended by the appended claims to cover modifications of the specific disclosed structure coming within the spirit and scope of this invention.

What is claimed:

1. A two-piece valve comprising:
   (a) a valve body having a longitudinal passage therethrough;
   (b) said valve body being formed of a rigid material;
   (c) said valve body including between the ends thereof an intermediate annular member extending inwardly from the wall of said passage and having a central opening therethrough;
   (d) said annular member including a transverse wall at one side thereof and a valve seat at the other side thereof, and having a predetermined longitudinal distance between said transverse wall and said valve seat;
   (e) a valve element of flexible elastic material received within said longitudinal passage and movable therein;
   (f) said valve element including an enlarged portion at one end, a valve-seat-engaging portion having a diameter greater than that of said central opening at the other end, and an intermediate portion of a diameter less than the diameter of said central opening;
   (g) said valve element being compressible so that said valve-seat-engaging portion may be forced through said opening in said annular member and said enlarged portion may be compressed against said transverse wall; and
   (h) the longitudinal distance between said transverse wall and said valve seat of said annular member exceeding the longitudinal distance between said enlarged portion and said valve seat-engaging portion of said valve element, whereby the resilience of said compressed enlarged portion urges said valve-seat-engaging portion firmly against said valve seat in sealing engagement.

2. The valve as recited in claim 1 wherein:
   (a) said longitudinal passage is formed at one end for receiving the tip a luer syringe; and
   (b) said enlarged portion of said valve element is engageable by the syringe to force said valve-seat-engaging portion of said valve element out of engagement with said valve seat to permit passage of fluid through the valve.

3. The valve element recited in claim 2 wherein said enlarged portion includes a transversely groove at the end thereof.

4. The valve as recited in claim 1 wherein said valve element has a portion of cruciform cross-section adjacent said transverse wall to provide longitudinal recesses for permitting passage of fluid between said valve element and said transverse wall.

5. The valve element as recited in claim 1 wherein said flexible elastic material of said valve element is silicone rubber.

6. The valve as recited in claim 1 wherein:

(a) said longitudinal distance between said transverse wall and said valve seat of said annular member is 0.88 inch; and (b) said longitudinal distance between said enlarged portion and said valve-seat-engaging portion of said valve element is 0.73 inch.

7. The valve as recited in claim 1 wherein said enlarged portion of said valve element has a diameter less than the diameter of said longitudinal passage in said valve body to provide space for passage of fluid between said valve body and said valve element.

8. The valve as recited in claim 3 wherein said transverse groove provides a path for flow of fluid from the syringe to the space between said enlarged portion of said valve element and said longitudinal passage in said valve body.

9. The valve as recited in claim 1 wherein said valve-seat-engaging portion of said valve element is formed to include a recess in the forward face thereof for facilitating compression of said valve-seat-engaging portion during assembly of said valve to permit passage of said valve-seat-engaging portion through said opening.

10. The valve as recited in claim 9 wherein said recess is cone-shaped and embraces an included angle of approximately 74°.

* * * * *